United States Patent [19]

Yanus et al.

[11] Patent Number: 4,521,621

[45] Date of Patent: Jun. 4, 1985

[54] NOVEL SQUARAINE SYSTEMS

[75] Inventors: John F. Yanus, Webster; William W. Limburg, Penfield, both of N.Y.

[73] Assignee: Xerox Corporation, Stamford, Conn.

[21] Appl. No.: 557,795

[22] Filed: Dec. 5, 1983

[51] Int. Cl.[3] ...................... C07C 85/00; C07C 85/02; C07C 85/06

[52] U.S. Cl. .................................................. 564/307

[58] Field of Search ........................................ 564/307

[56] References Cited

PUBLICATIONS

White et al., "J.A.C.S.", 86, pp. 453–458, 2/1964.

*Primary Examiner*—Paul F. Shaver

*Attorney, Agent, or Firm*—Peter H. Kondo; John E. Beck

[57] ABSTRACT

An unsymmetrical squaraine composition, process for synthesizing the unsymmetrical squaraine composition, devices containing the unsymmetrical squaraine composition, and methods of using the devices. The process for synthesizing the unsymmetrical squaraine composition comprises forming a mixture comprising squaric acid, a long chain primary alcohol, a first tertiary amine, and a second tertiary aromatic amine different from the first tertiary aromatic amine, and heating the mixture in vacuo below the boiling points of the primary alcohol, the first tertiary amine and the second tertiary aromatic amine to form an unsymmetrical squaraine composition. The novel unsymmetrical squaraine composition synthesized by this process may be used in electrostatographic imaging members comprising a supporting substrate and a photoconductive layer comprising the novel unsymmetrical squaraine composition. These electrostatographic imaging members may be utilized in an electrostatographic imaging processes.

7 Claims, No Drawings

NOVEL SQUARAINE SYSTEMS

BACKGROUND OF THE INVENTION

This invention relates in general to squaraines, and more specifically, to squaraine compositions of matter, process for preparing the squaraine compositions of matter, articles containing the squaraine compositions of matter and methods of using the articles containing the squaraine compositions of matter.

Squaraine compositions are useful for incorporation into photoresponsive devices to extend the response capability of such devices to visible light as well as infrared illumination. These photoresponsive devices can therefore be utilized, for example, in conventional electrophotographic copiers as well as in laser printers. These photoresponsive devices may comprise single or multilayered members containing photoconductive materials comprising squaraine compositions in a photogenerating layer, between a photogenerating layer and a hole transport layer, or between a photogenerating layer and a supporting substrate.

In one process for preparing squaraine compositions a dialkyl squarate can be reacted with an aniline compound. Thus, for example, in copending application Ser. No. 557,796, entitled Preparations of Squaraines Compositions, filed in the name of Kock Yee-Law concurrently herewith, a dialkyl squarate and an N,N-dialkyl aniline, in the presence of an acid catalyst, are reacted at a temperature of from about 80° C. to 160° C. Solvents, such as aliphatic alcohols, including methanol, ethanol, propanol, butanol, especially water saturated 1-butanol, amyl alcohol, are selected for the purpose of forming a solution of the squarate and the acid.

In still another process for preparing squaraine compositions squaric acid is reacted with a tertiary aromatic amine compound. Thus, for example, in copending application Ser. No. 557,801, entitled Process For Synthesizing Squaraine Compositions, filed in the name of John F. Yanus concurrently herewith, squaric acid, a long chain primary alcohol having a boiling point between about 130° C. and about 210° C. and a tertiary aromatic amine are heated in vacuo below the boiling points of the primary alcohol and the tertiary amine to form a squaraine composition.

Photoconductive imaging members containing certain squaraine compositions, including amine derivatives of squaric acid, are known. Also known are layered photoresponsive devices containing photogenerating layers and transport layers, as described, for example in U.S. Pat. No. 4,123,27, U.S. Pat. No. 4,353,971, U.S. Pat. No. 3,838,095, and U.S. Pat. No. 3,824,099. Examples of photogenerating layer compositions disclosed in U.S. Pat. No. 4,123,270 include 2,4-bis-(2-methyl-4-dimethylamino-phenyl)-1,3-cyclobutadiene-diylium-1,3-diolate, 2,4-bis-(2-hydroxy-4-dimethylamino-phenyl)-1,3-cyclobutadiene-diylium-1,3-diolate, and 2,4-bis-(p-dimethylamino-phenyl)-1,3-cyclobutadiene-diylium-1,3-diolate.

Although all the amine derivatives of squaraic acid described in U.S. Pat. No. 4,123,270, U.S. Pat. No. 4,353,971, U.S. Pat. No. 3,838,095, and U.S. Pat. No. 3,824,099 are symmetrical, a specific unsymmetrical, fused ring, nonamine derivative of squaric acid having hydroxy groups on a fused ring is disclosed in U.S. Pat. No. 4,353,971 and U.S. Pat. No. 3,824,099.

In Loutfy et al, "Photocoductivity of Organic Particle Dispersions: Squarine Dyes", Photographic Science and Engineering, Vol. 27, No. 1, January/February, 1982, pp 5-9, a structural formula of an amine derivative of squaric acid is illustrated on page 8 that is obviously a misprint in view of the text of the article.

The formation and development of electrostatic latent images on the imaging surface of photoconductive members by electrostatic means is well known. Generally, the method involves the formation of an electrostatic latent image on the surface of an electrophotographic plate, referred to in the art as a photoreceptor. This photoreceptor usually comprises a conductive substrate and one or more layers of photoconductive insulating material. A thin barrier layer may be interposed between the substrate and the photoconductive layer in order to prevent undesirable charge injection.

Many different photoconductive members are known including, for example, a homogeneous layer of a single material such as vitreous selenium, or a composite layered device containing a dispersion of a photoconductive composition. An example of one type of composite photoconductive member is described, for example, in U.S. Pat. No. 3,121,006. The composite photoconductive member of this patent comprises finely divided particles of a photoconductive inorganic compound dispersed in an electrically insulating organic resin binder. The photoconductive inorganic compound usually comprises zinc oxide particles uniformly dispersed in an electrically insulating organic resin binder coated on a paper backing. The binder materials disclosed in this patent comprise a material which is incapable of transporting for any significant distance injected charge carriers generated by the photoconductive particles. The photoconductive particles must therefore be in substantially contiguous particle to particle contact throughout the layer to permit the charge dissipation required for a cyclic operation. The uniform dispersion of photoconductive particles requires a relatively high volume concentration of photoconductor material, usually about 50 percent by volume, in order to obtain sufficient photoconductor particle to particle contact for rapid discharge. This high photoconductive particle loading can adversely affect the physical continuity of the resinous binder thereby significantly degrading the mechanical properties thereof. Specific binder materials disclosed in this patent include, for example, polycarbonate resins, polyester resins, polyamide resins, and the like.

Also known are photoreceptor materials comprising inorganic or organic materials wherein the charge carrier generating, and charge carrier transport functions are accomplished by discrete contiguous layers. Additionally, layered photoreceptor materials are disclosed in the prior art which include an overcoating layer of an electrically insulating polymeric material. However, the art of xerography continues to advance and more stringent demands need to be met by the electrostatographic imaging apparatus in order to improve performance, and to obtain higher quality images. Also desired are layered photoresponsive devices which are responsive to visible light and/or infrared illumination for certain laser printing applications.

Other layered photoresponsive devices including those comprising separate generating and transport layers are described, for example, in U.S. Pat. No. 4,265,990. Overcoated photoresponsive materials containing a hole injecting layer, overcoated with a hole transport layer, followed by an overcoating of a photogenerating layer, and an outer coating of an insulating organic resin are described, for example, in U.S. Pat. No. 4,251,612. Photogenerating layers disclosed in these patents include, for example, trigonal selenium and phthalocyanines and transport layers including certain diamines. The disclosures of U.S. Pat. Nos. 4,265,990 and 4,251,612 are incorporated herein by reference in their entirety.

There is also disclosed in Belgium Pat. No. 763,540, an electrophotographic member having at least two electrically operative layers, the first layer comprising a photoconductive layer which is capable of photogenerating charge carriers and injecting the carriers into a continuous active layer containing an organic transporting material which is substantially non-absorbing in the spectral region of intended use, but which is active in that it allows the injection of photogenerated holes from the photoconductive layer and allows these holes to be transported through the active layer. Additionally, there is disclosed in U.S. Pat. No. 3,041,116, a photoconductive material containing a transparent plastic material overcoated on a layer of vitreous selenium contained on a substrate.

While photoresponsive devices containing the above-described known squaraine materials are suitable for their intended purposes, there continues to be a need for the development of novel squaraine materals, improved processes for preparing the squaraine materials, and improved devices utilyzing the novel squaraine materials.

SUMMARY OF THE INVENTION

It is therefore an object of the present invention to provide improved processes for preparing squaraine compositions.

It is another object of the present invention, to provide improved an processes for preparing certain squaraine compositions with enhanced photosensitivity, excellent dark decay properties, and high charge acceptance.

It is yet another object of the present invention to provide a simpler, more rapid, more economical and higher yield process for preparing certain squaraine compositions.

It is another object of the present invention, to provide improved readily scaleable processes for preparing certain squaraine compositions.

It is still another object of the present invention to provide an improved photoresponsive imaging member containing novel squaraine compositions.

It is yet another object of the present invention to provide improved photoresponsive devices which exhibits low dark decay and greater sensitivity.

A further specific object of the present invention is the provision of an improved photoresponsive device comprising a photoconductive layer comprising novel squaraine photosensitive pigments and a hole transport layer.

In yet another embodiment of the present invention there are provided imaging and printing methods utilizing the improved photoresponsive device comprising a photoconductive layer comprising novel squaraine photosensitive pigments and a charge transport layer.

These and other objects of the present invention are accomplished by synthesizing an unsymmetrical squaraine composition comprising forming a mixture comprising squaric acid, a primary alcohol having a boiling point between about 130° C. and about 210° C., a first tertiary amine having the formula:

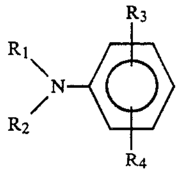

and a second tertiary amine having the formula:

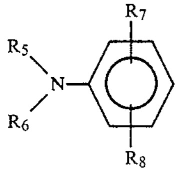

wherein $R_1$, $R_2$, $R_5$ and $R_6$ are independently selected from the group consisting of alkyl radicals having from 1 to 4 carbon atoms, phenyl radicals and radicals having the formula:

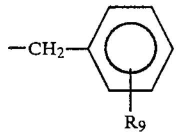

and $R_3$, $R_4$, $R_7$ and $R_8$ are independently selected from the group consisting of H, $CH_3$, $CH_2CH_3$, $CF_3$, F, Cl, Br, and COOH wherein at least one of $R_3$ and $R_4$ are different than $R_7$ and $R_8$ if $R_7$ and $R_8$ are located on the same relative position on the aromatic ring as $R_3$ and $R_4$ and wherein $R_9$ is selected from the group consisting of H, alkyl radicals having from 1 to 4 carbon atoms, F, Cl, Br, COOH, CN and $CF_3$, and heating the mixture in vacuo below the boiling points of the primary alcohol, the first tertiary amine and the second tertiary amine to form the unsymmetrical squaraine composition. Also considered within the scope of this invention is the novel unsymmetrical squaraine composition synthesized by this process; electrostatographic imaging members comprising a supporting substrate, a photoconductive layer comprising the novel unsymetrical squaraine composition; and methods of imaging with the electrostatographic imaging members comprising a supporting substrate and a photoconductive layer comprising the novel unsymmetrical squaraine composition.

The unsymmetrical squaraines of this invention have the structure embraced by the following formula:

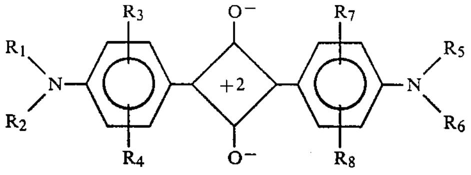

wherein $R_1$, $R_2$, $R_3$, $R_4$, $R_5$, $R_6$, $R_7$, $R_8$ and $R_9$ have already been defined above. Illustrative examples of specific novel squaraine compositions included within the scope of the present invention and embraced by the above formula include 2-(4-dimethylaminophenyl)-4-(2-methyl-4-dimethylaminophenyl)-1,3-cyclobutadienediylium-1,3-diolate, 2-(4-dimethylaminophenyl)-4-(2-fluoro-4-dimethylaminophenyl)-1,3-cyclobutadienediylium-1,3-diolate, 2-(2-methyl-4-dimethylaminophenyl)-4-(2-fluoro-4-dimethylamino-phenyl)-1,3-cyclobutadienediylium-1,3-diolate, 2-(2-fluoro-dimethylaminophenyl)-4-(3-fluoro-4-dimethylaminophenyl)-1,3-cyclobutadienediylium-1,3-diolate, 2-(-methyl-4-dimethylaminophenyl)-4-(2-chloro-4-dimethylaminophenyl)-1,3-cyclobutadienediylium-1,3-diolate, 2-(2-fluoro-4-dimethylaminophenyl)-4-(2-chloro-4-dimethylaminophenyl)-1,3-cyclobutadienediylium-1,3-diolate and the like.

The tertiary amine reactants may be selected from a wide variety of suitable materials. Typical tertiary amines include triaryl amines such as triphenyl amine, N,N'-diphenyl-N,N'-bis(3-methyl phenyl)-(1,1'-biphenyl)-4,4'-diamine, N,N'-diphenyl-N,N'-bis(4-methylphenyl)-(1,1'-biphenyl)-4,4'-diamine, heterocyclic amines such as N-ethylcarbazole and the like.

Tertiary aniline derivatives are preferred. Typical tertiary aniline derivatives include N,N-dimethylaniline, N,N-diethylaniline, N,N-dipropylaniline, N,N-dibutylaniline, N,N-dipentylaniline, N,N-dihexylaniline, 3-methyl-N,N-dimethylaniline, 3-fluoro-N,N-dimethylaniline, 3-hydroxy-N,N-diethylaninline, 3-ethyl-N,N-dimethylaniline 3-chloro-N,N-dimethylaniline, 2-fluoro-N,N-dimethylaniline, 2-methyl-N,N-dimethylaniline, 2-trifluoromethane-N,N-dimethylaniline, 2-N,N,-trifluoromethane-N,N-dimethylaniline, N,N-dimethylamino-3-fluorobenzene, N-methyl-N-ethyl-3-fluoroaniline, N,N-diethyl-3-fluoroaniline, N,N-dibenzyl-3-fluoroaniline, N-methyl-N-benzyl-3-fluoroaniline, N,N-di(4-chlorophenylmethyl)-3-fluoroaniline and the like.

The squaric acid reactant is also known as 1,2-dihydroxy-3,4-cyclobutenediol.

A primary alcohol having a boiling point between about 130° C. and about 210° C. must be employed to form the solution of squaric acid and tertiary amine reactants. Typical alcohols having boiling points within this range include heptanol, octanol, nonanol, decanol, branched primary alcohols such as 2-ethyl-1-hexanol, and alcohol mixtures such as Soltrol 130® (a mixture of branched aliphatic hydrocarbons $C_{11}$–$C_{13}$ having a boiling point of approximately 175°–180° C., available from Phillips Chemical Co.). Higher boiling point alcohols such as nonanol and decanol may be mixed with lower boiling point alcohols to ensure the presence of an alcohol having a boiling point less than the boiling point of the tertiary amine employed in the reaction. 1-heptanol and 2-ethyl-1-hexanol are preferred because the squaraine synthesis reaction can be more readily scaled up with reduced competive reactions. Since the reaction is carried out under vacuum, improved results are achieved with a greater difference in boiling point between water and the alcohol. The more volatile water separates much more readily from heptanol than from butanol. Moreover, the solubility of water in heptanol is much less than butanol. Also, there are reduced side reactions because the larger heptanol molecule is less likely to form the diester than butanol. The boiling point of heptanol is 176° C. Since the reaction involves removal of water/alcohol during refluxing, the boiling point of the alcohol must normally be less than the boiling point of the tertiary amine, e.g. the boiling point of dimethyl aniline is 193° C. However, if a mixture of alcohols are used, at least one of the alcohols in the mixture should have a boiling point between about 130° C. and about 210° C. and have a boiling point less than the boiling point of the tertiary amine. Sufficient long chain aliphatic alcohol having a boiling point between about 130° C. and about 210° C. should be present in the reaction mixture to maintain the desired pressure and temperature during refluxing. A long chain aliphatic alcohol having a boiling point between about 170° C. and about 185° C. is preferred because the higher reaction temperatures drive off the water more rapidly without exceeding the boiling point of the tertiary amine. Secondary alcohols provide poor yields and tertiary alcohols fail to provide any reaction product at all.

Alcohol solvents, such as lower boiling point aliphatic alcohols such as methanol, ethanol, propanol, butanol, 1-butanol, amyl alcohol are avoided in the process of this invention because of side reactions, high solubility of water in these alcohols and poor yields. For example, no yield is obtained with butanol/benzene or butanol/toluene solvents for reaction batches of 0.5 mole or greater.

The reaction may, if desired, be carried out in the presence of any suitable strong acid. Typical strong acids include various inorganic acids and organic acids such as sulfuric acid, trichloroacetic acid, dichloroacetic acid, trichloroacetic acid, oxalic acid, 2,2,2-trifluoroethanol, toluene sulfonic acid, and the like. Sulfuric acid and trichloroacetic are preferred. Excellent results have been obtained with trichloroacetic acid at a $pK_a$ of about 2.85. Generally, satisfactory results are obtained with a $pK_a$ of less than about 3 to 4. The dark decay of the squaraine reaction product is improved when a strong acid is employed.

The reaction temperature and pressure can vary over a relatively wide range, and is generally dependent on the alcohols and tertiary amines used. The reaction temperature and pressure should be regulated to prevent boiling of the the primary alcohol and tertiary amines. Depending upon the materials employed, the reaction temperature is generally maintained between about 60° C. and about 130° C. and the pressure is generally maintained between about 5 torr and about 200 torr. Thus, for example, the pressure is normally held at about 10 torr at about 75° C. and held at about 43 torr at about 110° C. when 2-ethyl-1-hexanol is used.

The reaction times are generally dependent on the reaction temperature, solvent and tertiary amines used.

The reaction is conducted with refluxing and the water formed during the reaction may be removed by conventional techniques employing devices such as a Dean-Stark trap.

The proportion of reactants, primary alcohol, and acid employed is not critical and depends upon a number of factors including, for example, the specific reactants used, the pressure, and the reaction temperature. Generally, however, satisfactory results may be achieved by utilyzing with 1 mole of squaric acid, about 1 mole to about 1.2 moles of each tertiary amine, and from about 2 liters to about 12 liters of primary alcohol, particularly for tertiary amines having similar reaction rates with squaric acid. However, where the different tertiary amines in a given reaction mixture have vastly different reaction rates with squaric acid, a greater proportion of the less reactive tertiary amine may be used. As indicated above, a strong acid may also be added to the reaction mixture. For example, excellent results have been achieved with between about 2 liters and about 12 liters of 2-ethyl-hexanol per mole of squaric acid. Generally, it is desirable to minimize the amount of solvent used to minimize the amount of solvent that must be filtered off after completion of the reaction. However, when the proportion of solvent to squaric acid is reduced below about 2 liters of primary alcohol to 1 mole of squaric acid, stirring becomes more difficult. All reactants may be added at about the same time or sequentially.

The resulting product may be separated from the reaction mixture by conventional techniques, such as filtration, washed with any suitable washing liquid such as methanol, ethanol, acetone and the like and dried by conventional means such as oven driers.

The reaction products comprise both unsymmetrical and symmetrical squaraines which were identified primarily by melting point data, infrared analysis, $C^{13}$ and proton nuclear resonance, mass spectroscopy and visible absorption spectroscopy. Also, elemental analysis for the respective substituents, such as analysis for carbon, hydrogen, nitrogen, and fluorine was performed. The data generated from analysis was compared with the data available for identical compounds prepared from squaric acid reactions processes using lower alcohol solvents and compared with the data available for identical compounds prepared from squarate reactions. The proportion of unsymmetrical and symmetrical squaraines in the reaction product varies with the type and relative amounts of each tertiary aniline derivative used. The reaction product containing both unsymmetrical and symmetrical squaraines may be used as a mixture in an electrostatographic imaging member or the unsymmetrical squaraine may be separated from the other reaction products and thereafter utilized in an electrostatographic imaging member.

In one embodiment, the process of the present invention involves forming a mixture from about 1 mole of squaric acid with from about 1 mole to about 0.2 mole of one tertiary aniline derivative, about 1.5 moles to about 2.3 moles of another tertiary aniline derivative, and from about 2 liters to about 12 liters of primary alcohol having a boiling point between about 130° C. and about 190° C. This mixture was heated to a temperature of from about 75° C. and about 110° C. with continual stirring while the pressure is maintained between about 10 torr and about 43 torr. The reaction mixture was allowed to cool and the desired reaction product was isolated by filtration from the reaction mixture. The resulting products were of small particle size, ranging from about 1 micrometer to about 25 micrometers.

The squaraine compositions prepared in accordance with the process of the present invention are useful as photoconductive substances. In one embodiment, they can be employed in a layered photoresponsive device comprising a supporting substrate, a photoconducting layer comprising the squaraine compositions prepared in accordance with the present invention, and a charge transport layer. In another embodiment, the photoresponsive device comprises a substrate, a charge transport layer, and a photoconducting layer comprising the squaraine compositions prepared in accordance with the process of the present invention. In still another embodiment, photoresponsive devices useful in printing systems be prepared in which the devices comprise a layer of the squaraine photoconductive composition prepared in accordance with the process of the present invention positioned between a photogenerating layer and a hole transport layer or wherein the squaraine photoconductive squaraine composition layer is positioned between a photogenerating layer and a supporting substrate. In the latter devices, the photoconductive layer comprising the squaraine compositions serves to enhance or reduce the intrinsic properties of the photogenerating layer in the infrared and/or visible range of the spectrum.

One specific improved photoresponsive device utilizing the squaraines prepared in accordance with the process of the present invention comprises a supporting substrate; a hole blocking layer; an optional adhesive interface layer; an inorganic photogenerator layer; a photoconductive composition layer comprising the squaraine materials prepared in accordance with the process of the present invention; and a hole transport layer.

The photoresponsive devices described can be prepared by any suitable well known method, the process parameters and the order of coating of the layers being dependent on the device desired. Thus, for example, a three layered photoresponsive device can be prepared by deposition of the photoconducting layer on a supporting substrate and subsequently depositing a charge transport layer. In another process variant, the layered photoresponsive device can be prepared by providing a conductive substrate having a blocking layer and an optional adhesive layer, and thereafter applying thereto a photoconducting layer. The photoconducting layer comprising the novel squaraines of the present invention as well as the transport layer can be formed by solvent coating processes, laminating processes, or other suitable processes.

The improved photoresponsive devices of the present invention can be incorporated into various imaging systems such as conventional xerographic imaging copying and printing systems. Additionally, the improved photoresponsive devices of the present invention containing an inorganic photogenerating layer and a photoconductive layer comprising the squaraines of the present invention can function simultaneously in imaging and printing systems with visible light and/or infrared light. In this embodiment, the improved photoresponsive devices of the present invention may be negatively charged, exposed to light in a wavelength of from about 400 to about 1,000 nanometers, either sequentially or simultaneously, followed by developing the resulting image and transferring the image to paper. The above sequence may be repeated many times.

Exposure to illumination and erasure of the layered photoresponsive devices of the present invention may be effected from either side of the devices or combinations thereof depending on the degree of transparency of any intervening layers between the source of activating radiation and the photoconductive layer.

The charge transport layer may be positioned between the supporting substrate and the photoconductive layer. More specifically the photoresponsive device may comprise a supporting substrate, a hole transport layer comprising a hole transport composition dispersed in an inert resinous binder composition, and a photoconductive layer, comprising the novel squaraine compositions of the present invention alone or optionally dispersed in a resinous binder composition.

Alternatively, the improved photoresponsive device of the present invention may comprise a substrate, a hole blocking metal oxide layer, an optional adhesive layer, a charge carrier inorganic photogenerating layer, an organic photoconductive composition layer comprising the novel squaraine compositions of the present invention, and a hole transport layer. The inorganic photogenerating layer, the organic photoconductive layer, and the hole transport layer, are generally dispersed in resinous binder compositions. Thus, for example, the inorganic photogenerating layer may comprise an inorganic photogenerating composition dispersed in an inactive resin binder.

Alternatively the photoconductive layer may be positioned between the inorganic photogenerating layer and the substrate, and more specifically, the photoconductive layer in this embodiment may be located between the optional adhesive layer and the inorganic photogenerating layer.

One preferred photoresponsive device of the present invention comprises a substrate comprising a Mylar web having a thickness of about 3 mils coated with a layer of 20 percent light transmissive aluminum having a thickness of about 100 Angstroms, a metal oxide layer comprising aluminum oxide having a thickness of about 20 Angstroms, a polyester adhesive layer (available from E. I. duPont de Nemours & Co. as 49,000 Polyester) having a thickness of about 0.05 microns, a photogenerating layer having a thickness of about 0.5 micron and comprising about 30 percent by weight of squaraine dispersed in about 70 percent by weight of resinous binder, and a hole transport layer having a thickness of about 25 microns and comprising about 50 weight percent of N,N'-diphenyl-N,N'-bis(3-methylphenyl)-[1,1'-biphenyl]-4,4'-diamine, dispersed in a polycarbonate resin binder.

In a further embodiment of the photoresponsive device of the present invention comprises a substrate comprising a Mylar web having a thickness of about 3 mils coated with about a 100 Angstrom layer of 20 percent light transmissive aluminum, a metal oxide hole blocking layer of aluminum oxide having a thickness of about 20 Angstroms, an optional adhesive layer (available from E. I. duPont de Nemours & Co. as 49,000 Polyester) having a thickness of about 0.05 micron, a photogenerating layer comprising about 33 volume percent of trigonal selenium dispersed in a phenoxy resinous binder (available from Allied Chemical Corporation as the poly(hydroxyether) Bakelite) and having a thickness of about 0.4 micron, a photoconductive layer about 30 percent by volume of the reaction product of squaric acid, dimethylaniline and N,N-dimethyl-m-toluidine containing unsymmetrical squaraine dispersed in about 70 percent by volume resinous binder (available as Formvar ® from Monsanto Company) having a thickness of about 0.5 micron, and a hole transport layer having a thickness of about 25 microns comprising about 50 percent by weight of N,N'-diphenyl-N,N'-bis(3-methylphenyl)-[1,1'-biphenyl]-4,4'-diamine, dispersed in about 50 percent by weight of a polycarbonate resinous binder.

The substrate layers may be opaque or substantially transparent and may comprise any suitable material having the requisite mechanical properties. Thus the substrate may comprise a layer of insulating material such as an inorganic or organic polymeric material such as Mylar, a commercially available polymer; a layer of an organic or inorganic material having a semi-conductive surface layer such as indium tin oxide, or aluminum, or a conductive material such as, for example, aluminum, chromium, nickel, brass or the like. The substrate may be flexible or rigid and many have any suitable configuration, such as, for example, a plate, a cylindrical drum, a scroll, an endless flexible belt and the like. If desired, the rear surface of the substrate may be coated with an anti-curl layer, such as for example, resin materials.

The thickness of the substrate layer is not particularly critical. Depending on such factors as economical considerations, this layer may be of substantial thickness, for example, over 100 mils or even may be eliminated if the remainder of the photoresponsive device is self supporting. A belt thickness of from about 75 micrometers to about 250 micrometers is satisfactory for high speed machines.

The hole blocking layers may comprise any suitable known materials such as metal oxides including aluminum oxide and indium tin oxide; resins such as polyvinyl butyral; polymeric organo silanes derived from silicon compounds such as hydrolyzed 3-aminopropyltriethoxy silane; organo metallic compounds such as metal acetyl acetonates; and the like. The primary purpose of this layer is to provide charge blocking, that is to prevent charge injection from the substrate during and after charging. Typically, this layer has a thickness of less than about 50 Angstroms.

Any suitable adhesive layer may be employed. Typical adhesive layers include polymeric material such as polyesters, polyvinyl butyral, polyvinyl pyrrolidone and the like. Typically, this layer has a thickness of less than about 0.3 micron.

The inorganic photogenerating layer may comprise any suitable photoconductive charge carrier generating material sensitive to visible light. Typical inorganic photogenerating materials include amorphous selenium, amorphous selenium alloys, halogen doped amorphous selenium, halogen doped amorphous selenium alloys, trigonal selenium, mixtures of alkali metal selenite and carbonates with trigonal selenium, cadmium sulphide, cadmiun selenide, cadmium telluride, cadmium sulfur selenide, cadmiun sulfur telluride, cadmium seleno telluride, copper, and chlorine doped cadmium sulphide, cadmium selenide and cadmium sulphur selenide and the like. Typical alloys of selenium include selenium tellurium alloys, selenium arsenic alloys, selenium tellurium arsenic alloys, and such alloys additionally containing a halogen material such as chlorine in an amount of from about 50 to about 200 parts per million.

The inorganic photogenerating layer typically has a thickness of from about 0.05 micron to about 10 microns or more, and preferably from about 0.4 micron to about 3 microns. However, the thickness of this layer is primarily dependent on the volume loading of the photoconductive material, which may vary from about 5 to about 100 volume percent. Generally, it is desirable to provide this layer in a thickness which is sufficient to absorb about 90 percent or more of the incident radiation which is directed upon it in the imagewise or printing exposure step. The maximum thickness of this layer is dependent primarily upon physical factors such as mechanical considerations, e.g. whether a flexible photoresponsive device is desired.

A very important layer of the photoresponsive device of the present invention is a photoconductive layer comprising the novel squaraine compositions disclosed herein. These compositions are generally electronically compatible with the charge carrier transport layer in order that photoexcited charge carriers can be injected into the transport layer and further in order that charge carriers can travel in both directions across the interface between the photoconductive layer and the charge transport layer.

Generally, the thickness of the photoconductive layer depends on a number of factors including the thicknesses of the other layers and the proportion of photoconductive material contained in this layer. Accordingly, this layer can range in thickness of from about 0.05 micron to about 10 microns when the photoconductive squaraine composition of this invention is present in an amount of from about 5 percent to about 100 percent by volume. More preferably, this layer should range in thickness between about 0.25 micron to about 1 micron when the photoconductive squaraine composition is present in this layer in an amount of about 30 percent by volume. The maximum thickness of this layer is dependent primarily upon physical factors such as mechanical considerations, e.g. whether a flexible photoresponsive device is desired.

The inorganic photogenerating materials or the photoconductive materials can comprise 100 percent of the respective layers or these materials can be dispersed in various suitable inorganic or resinous polymer binder materials in amounts of from about 5 percent by volume to about 95 percent by volume. Illustrative examples of polymeric binder resins that can be selected include those disclosed, for example, in U.S. Pat. No. 3,121,006, the disclosure of which is incorporated herein by reference in its entiret. Typical polymeric binder resins materials include polyesters, polyvinyl butyral, polycarbonate resins, polyvinyl carbazole, epoxy resins, poly(hydroxyether) resins, and the like.

The charge carriers transport layers may comprise any suitable material which is capable of efficiently transporting charge carriers. This layer generally has a thickness in the range of from about 5 microns to about 50 microns. A thickness of about 20 micrometers is preferred because such layer thickness is more efficient and wear resistant than thinner layers having lower mobility carrier transport molecules. In a particularly preferred embodiment, the transport layer comprises diamine molecules of the formula:

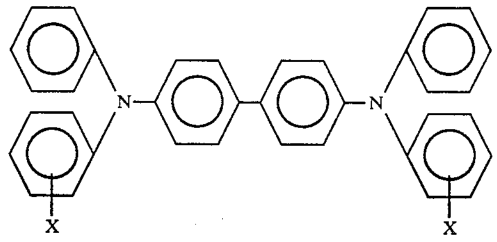

dispersed in a highly insulating and transparent organic resinous binder wherein X is selected from the group consisting of (ortho) $CH_3$, (meta) $CH_3$, (para) $CH_3$, (ortho) Cl, (meta) Cl, (para) Cl. The highly insulating resin, which has a resistivity of at least about $10^{12}$ ohm-cm to prevent undue dark decay, is a material which is not necessarily capable of supporting the injection of holes from the photogenerating layer and is not capable alone of allowing the transport of these holes through the material. However, the resin becomes electrically active when it contains from about 10 to 75 weight percent of the substituted diamines corresponding to the foregoing formula.

Compounds corresponding to the above formula include, for example, N,N'-diphenyl-N,N'-bis(alkylphenyl)-[1,1-biphenyl]-4,4'-diamine wherein the alkyl is selected from the group consisting of methyl such as 2-methyl, 3-methyl and 4-methyl, ethyl, propyl, butyl, hexyl and the like. In the case of chloro substitution, the compound is N,N'-diphenyl-N,N'-bis(chlorophenyl)-[1,1'-biphenyl]-4,4'-diamine wherein the chloro atom is 2-chloro, 3-chloro or 4-chloro.

Other electrically active small molecules which can be dispersed in the electrically inactive resin to form a layer which will transport holes include, for example, bis(4-diethylamine-2-methylphenyl)phenylmethane; 4',4''-bis(diethylamino)-2'2''-dimethyltriphenyl methane; bis-4 (diethylaminophenyl)phenylmethane; and 4,4'-bis(diethylamino)-2,2'-dimethyltriphenylmethane. Providing that the objectives of the present invention are achieved, other suitable charge carrier transport molecules can be employed in the transport layer.

Examples of the highly insulating and transparent resinous material or inactive binder resinous material, for the transport layers include materials such as those described in U.S. Pat. No. 3,121,006 the disclosure of which is incorporated herein by reference in its entirety. Specific examples of organic resinous materials include polycarbonates, acrylate polymers, vinyl polymers, cellulose polymers, polyesters, polysiloxanes, polyamides, polyurethanes and epoxies as well as block, random or alternating copolymers thereof. Preferred electrically inactive binder materials are polycarbonate resins having a molecular weight (Mw) of from about 20,000 to about 100,000 with a molecular weight in the range of from about 50,000 to about 100,000 being particularly preferred. Generally, the resinous binder contains from about 10 to about 75 percent by weight of the active transport material and more preferably from about 35 percent to about 50 percent based on the total weight of the transport layer.

With more specific reference to the three layered devices comprising a supporting substrate, a hole transport layer, and a photoconductive layer, the supporting substrate layer may be opaque or substantially transparent and may comprise a suitable material having the requisite mechanical properties. This substrate may comprise a layer of insulating material such as an inorganic or organic polymeric material, a layer of an organic or inorganic material having a conductive surface layer thereon, or a conductive material such as, for example, aluminum, chromium, nickel, indium, tin oxide, brass or the like. Also, optional layers known hole blocking layers such as aluminum oxide and adhesive materials such as a polyester resin can be coated on the substrate. The substrate may be flexible or rigid and may have any of many different configurations, such as for example, a plate, a cylindrical drum, a scroll, an endless flexible belt and the like. Preferably, this substrate is in the form of an endless flexible belt. When in the configuration of a belt, in some instances it may be desirable to apply a coating of an adhesive layer to the selected substrate subsequent to the formation of a hole blocking layer, such as aluminum oxide.

The photoconductive layers comprise the novel squaraine compositons of the present invention optionally dispersed in a resinous binder composition. These squaraines are electronically compatible with the charge transport layer and therefore allow the photoexcited charge carriers to be injected into the transport layer and allowing charge carriers to travel in both directions across the interface between the charge transport layer and the photogenerating layer.

The photoconductive squaraine pigments of the present invention are preferably dispersed in a binder material, such as various suitable inorganic or organic binder compositions, in amounts of from about 5 percent by volume to 95 percent by volume. An amount of from about 25 percent by volume to about 75 percent by volume of the photoconductive squaraine pigment is preferred because the carrier generator layer should efficiently absorb a large percentage of the incident light. Also, in the absence of other carrier transport molecules in the charge generator layer, particle contact of the generator pigments is required to transport charge to the transport layer and the counter ion to the ground plane. Illustrative examples of polymeric resinous binder materials that can be selected include those disclosed, for example, in U.S. Pat. No. 3,121,006, the disclosure of which is incorporated herein by reference in its entirety. Typical polymeric resinous binder materials include polyesters, polyvinylbutyral, Formvar®, polycarbonate resins, polyvinyl carbazoles, epoxy resins, phenoxy resins commercially available as poly(hydroxyether) resins, and the like.

Also included within the scope of the present invention are methods of imaging with the photoresponsive devices containing the novel squaraines of this invention. These methods of imaging generally involve the formation of an electostatic latent image on the imaging member, development of the image with a developer composition, and transfer of the image to suitable reciving member and permanently affixing the image thereto. The electrostatic latent image may be formed by any suitable technique such as by uniform electrostatic charging followed by exposure to activating radiation. Exposure to activating radiation may be effected by means of a conventional light/lens system using a broad spectrum white light source or by other means such as a laser or image bar. In the later two embodiments the photoresponsive device is sensitive to infrared illumination.

The invention will now be described in detail with reference to specific preferred embodiments thereof, it being understood that these examples are intended to be illustrative only. The invention is not intended to be limited to the materials, conditions, or process parameters recited herein. All parts and percentages are by weight unless otherwise indicated.

EXAMPLE I

Into a 1000 milliliter three-necked round bottom flask equipped with a mechanical stirrer, thermometer and a condenser with a Dean-Stark trap was placed 5.7 grams squaric acid (0.05 mole), 12.5 grams N,N-dimethyl-3-chloroaniline (0.8 mole) and 300 milliliters 2-ethyl-1-hexanol. A vacuum of 25 Torr was applied by means of a gas inlet connecting tube at the top of the condenser. The mixture was heated with stirring to reflux at 95° C. for one hour. The vacuum was broken and 8.5 grams N,N-dimethyl-3-fluoroaniline (0.61 mole) was added to the green solution. The vacuum was reapplied and the reaction continued for 12 hours. The mixture was cooled and filtered. The blue crystalline pigment was washed with methanol and dried in vacuo at 50° C. Yield was 8.7 grams.

EXAMPLE II

A siloxane layer was formed on an aluminized polyester film, Mylar®, in which the aluminum had a thickness of about 150 Angstroms by applying a 0.22 percent (0.001 mole) solution of 3-aminopropyl triethoxylsilane to the aluminum layer with a Bird applicator. The deposited coating was dried in a forced air oven to form a dried coating having a thickness of 200 Angstroms. A coating of polyester resin, du Pont 49000, available from E. I. duPont de Nemours & Co. was then applied with a Bird applicator to the dried silane layer. The polyester resin coating was dried to form a film having a thickness of about 0.5 micrometer. About 0.075 gram of the blue crystalline squaraine pigment of Example I was mixed in about 0.15 gram of a binder of Makrolon®, (polycarbonate resin available from Farbenfabricken Bayer A.G.) and sufficient methylene chloride to form a 15 percent solids mixture. This mixture applied by means of a Bird applicator having a 0.5 mil gap to the polyester resin coating to form a coating. After drying in a forced air oven for 5 minutes at temperature of 135° C., the dried coating was found to have a thickness of about 0.5 micrometer. This squaraine generating layer was then overcoated with a methylene chloride solution containing 15 percent solids, the solids containing about 50 percent by weight N,N'-diphenyl-N,N'-bis(3-methylphenyl)-1,1'-biphenyl-4,4'-diamine dispersed in about 50 percent by weight of Makrolon® (polycarbonate resin available from Farbenfabricken Bayer A.G.) and then dried at 135° C. for 5 minutes. The charge transport layer had a thickness of 32 micron after drying. Electrical evaluation of the resulting coated device charged to about −1000 to −1200 volts revealed a dark decay of about 80 volts per second. Discharge when exposed to 10 ergs of activating radiation at a wavelength of about 800 nanometers was about 70 percent.

EXAMPLE III

Into a 1000 milliliter three-necked round bottom flask equipped with a mechanical stirrer, thermometer and a condenser with a Deak-Stark trap was placed 11.4 grams squaric acid (0.1 mole), 33 grams N,N-dimethyl-3-fluoroaniline (0.24 mole) and 400 milliliters 1-heptanol. A vacuum of 36 Torr was applied by means of a gas inlet connecting tube at the top of the condenser. The mixture was heated with stirring to reflux at 100° C. The water formed during the course of the reaction was allowed to collect in the Dean-Stark trap. After 20 hours, the reaction was allowed to cool and was filtered. The blue crystalline pigment was washed with methanol and dried in vacuo at 50° C. Yield was 23 grams, 59 percent.

EXAMPLE IV

A siloxane layer was formed on an aluminized polyester film, Mylar, in which the aluminum had a thickness of about 150 Angstroms by applying a 0.22 percent (0.001 mole) solution of 3-aminopropyl triethoxylsilane to the aluminum layer with a Bird applicator. The deposited coating was dried in a forced air oven to form a dried coating having a thickness of 200 Angstroms. A coating of polyester resin, du Pont 49000, available from E. I. du Pont de Nemours & Co. was then applied with a Bird applicator to the dried silane layer. The polyester resin coating was dried to form a film having a thickness of about 0.5 micrometer. About 0.075 gram of the blue crystalline squaraine pigment of Example III was mixed in about 0.15 gram of a binder of Makrolon®, (polycarbonate resin available from Farbenfabricken Bayer A.G.) and sufficient methylenechloride to form a 15 percent solids mixture. This mixture applied by means of a Bird applicator having a half mil gap to the polyester resin coating to form a coating. After drying in a forced air oven for 5 minutes at temperature of 135° C., the dried coating was found to have a thickness of about 0.5 micrometer. This squaraine generating layer was then overcoated with a charge transport layer containing about 50 percent by weight N,N'-diphenyl-N,N'-bis(3-methylphenyl)-1,1'-biphenyl-4,4'-diamine dispersed in about 50 percent by weight of Makrolon ® (polycarbonate resin available from Farbenfabricken Bayer A.G.). The charge transport layer had a thickness of 32 micron after drying. Electrical evaluation of the resulting coated device charged to about −1000 to −1200 volts revealed a dark decay of about 500+ volts per second. The rate of dark decay was too high to allow measurement of sensitivity.

EXAMPLE V

Into a 1000 milliliter three-necked round bottom flask equipped with a mechanical stirrer, thermometer and a condenser with a Dean-Stark trap was placed 5.7 grams squaric acid (0.05 mole), 12.8 grams N,N-dimethylaniline (0.106 moles), 2.5 grams N,N-dimethyl-m-toluidine (0.019 mole) and 300 milliliters 2-ethyl-1-hexanol. A vacuum of 20 Torr was applied by means of a gas inlet connecting tube at the top of the condenser. The mixture was heated with stirring to reflux at 90° C. The water formed during the course of the reaction was allowed to collect in the Dean-Stark trap. After 24 hours, the reaction was allowed to cool and was filtered. The blue crystalline pigment was washed with methanol and dried in vacuo at 50° C. Yield was 13.1 grams.

EXAMPLE VI

A siloxane layer was formed on an aluminized polyester film, Mylar, in which the aluminum had a thickness of about 150 Angstroms by applying a 0.22 percent (0.001 mole) solution of 3-aminopropyl triethoxylsilane to the aluminum layer with a Bird applicator. The deposited coating was dried in a forced air oven to form a dried coating have a thickness of 200 Angstroms. A coating of polyester resin, du Pont 49000, availble from E. I. du Pont de Nemours & Co. was then applied with a Bird applicator to the dried silane layer. The polyester resin coating was dried to form a film having a thickness of about 0.5 micrometer. About 0.075 gram of the blue crystalline squaraine pigment of Example V was mixed in about 0.15 gram of a binder of Makrolon ®, (polycarbonate resin available from Farbenfabricken Bayer A.G.) and sufficient methylene chloride to form a 15 percent solids mixture. This mixture applied by means of a Bird applicator having a half mil gap to the polyester resin coating to form a coating. After drying in a forced air oven for 5 minutes at temperature of 135° C., the dried coating was found to have a thickness of about 0.5 micrometer. This squaraine generating layer was then overcoated with a charge transport layer containing about 50 percent by weight N,N'-diphenyl-N,N'-bis(3-methylphenyl)-1,1'-biphenyl-4,4'-diamine dispersed in about 50 percent by weight of Makrolon ® (polycarbonate resin available from Farbenfabricken Bayer A.G.). The charge transport layer had a thickness of 32 micron after drying. Electrical evaluation of the resulting coated device charged to about −1000 to −1200 volts revealed a dark decay of about 120 volts per second. Discharge when exposed to 10 ergs of activating radiation at a wavelength of about 800 nanometers was about 55 percent.

EXAMPLE VII

Into a 1000 milliliter three-necked round bottom flask equipped with a mechanical stirrer, thermometer and a condenser with a Dean-Stark trap was placed 5.7 grams squaric acid (0.05 mole), 11.4 grams N,N-dimethylaniline (0.093 mole), 4.2 grams N,N-dimethyl-m-toluidine (0.0313 mole) and 300 milliliters 2-ethyl-1-hexanol. A vacuum of 20 Torr was applied by means of a gas inlet connecting tube at the top of the condenser. The mixture was heated with stirring to reflux at 90° C. The water formed during the course of the reaction was allowed to collect in the Dean-Stark trap. After 24 hours, the reaction was allowed to cool and was filtered. The blue crystalline pigment was washed with methanol and dried in vacuuo at 50° C. Yield was 13.6 grams.

EXAMPLE VIII

A siloxane layer was formed on an aluminized polyester film, Mylar, in which the aluminum had a thickness of about 150 Angstroms by applying a 0.22 percent (0.001 mole) solution of 3-aminopropyl triethoxylsilane to the aluminum layer with a Bird applicator. The deposited coating was dried in a forced air oven to form a dried coating having a thickness of 200 Angstroms. A coating of polyester resin, du Pont 49000, available from E. I. du Pont de Nemours & Co. was then applied with a Bird applicator to the dried silane layer. The polyester resin coating was dried to form a film having a thickness of about 0.5 micrometer. About 0.075 gram of the blue crystalline squaraine pigment of Example VII was mixed in about 0.15 gram of a binder of Makrolon ®, (polycarbonate resin available from Farbenfabricken Bayer A.G.) and sufficient methylene chloride to form a 15 percent solids mixture. This mixture applied by means of a Bird applicator having a half mil gap to the polyester resin coating to form a coating. After drying in a forced air oven for 5 minutes at temperature of 135° C., the dried coating was found to have a thickness of about 0.5 micrometer. This squaraine generating layer was then overcoated with a charge transport layer containing about 50 percent by weight N,N'-diphenyl-N,N'-bis(3-methylphenyl)-1,1'-biphenyl-4,4'-diamine dispersed in about 50 percent by weight of Makrolon ® (polycarbonate resin available from Farbenfabricken Bayer A.G.). The charge transport layer had a thickness of 32 micron after drying. Electrical evaluation of the resulting coated device charged to about −1000 to −1200 volts revealed a dark decay of about 40 volts per second. Discharge when exposed to 10 ergs of activating radiation at a wavelength of about 800 nanometers was about 68 percent.

EXAMPLE IX

Into a 1000 milliliter three-necked round bottom flask equipped with a mechanical stirrer, thermometer and a condenser with a Dean-Stark trap was placed 5.7 grams squaric acid (0.05 mole), 7.6 grams N,N-dimethylaniline (0.0625 mole), 8.4 grams N,N-dimethyl-m-toluidine and 300 milliliters 2-ethyl-1-hexanol. A vacuum of 20 Torr was applied by means of a gas inlet connecting tube at the top of the condenser. The mixture was heated with stirring to reflux at 90° C. The water formed during the course of the reaction was allowed to collect in the Dean-Stark trap. After 20 hours, the reaction was allowed to cool and was filtered. The blue crystalline pigment was washed with methanol and dried in vacuuo at 50° C. Yield was 13.8 grams.

EXAMPLE X

A siloxane layer was formed on an aluminized polyester film, Mylar, in which the aluminum had a thickness of about 150 Angstroms by applying a 0.22 percent (0.001 mole) solution of 3-aminopropyl triethoxylsilane to the aluminum layer with a Bird applicator. The deposited coating was dried in a forced air oven to form a dried coating having a thickness of 200 Angstroms. A coating of polyester resin, du Pont 49000, available from E. I. du Pont de Nemours & Co. was then applied with a Bird applicator to the dried silane layer. The polyester resin coating was dried to form a film having a thickness of about 0.5 micrometer. About 0.075 gram of the blue crystalline squaraine pigment of Example IX was mixed in about 0.15 gram of a binder of Makrolon ®, (polycarbonate resin available from Farbenfabricken Bayer A.G.) and sufficient methylene chloride to form a 15 percent solids mixture. This mixture applied by means of a Bird applicator having a half mil gap to the polyester resin coating to form a coating. After drying in a forced air oven for 5 minutes at temperature of 135° C., the dried coating was found to have a thickness of about 0.5 micrometer. This squaraine generating layer was then overcoated with a charge transport layer containing about 50 percent by weight N,N'-diphenyl-N,N'-bis(3-methylphenyl)-1,1'-biphenyl-4,4'-diamine dispersed in about 50 percent by weight of Makrolon ® (polycarbonate resin available from Farbenfabricken Bayer A.G.). The charge transport layer had a thickness of 32 micron after drying. Electrical evaluation of the resulting coated device charged to about −1000 to −1200 volts revealed a dark decay of about 20 volts per second. Discharge when exposed to 10 ergs of activating radiation at a wavelength of about 800 nanometers was about 45 percent.

EXAMPLE XI

Into a 1000 milliliter three-necked round bottom flask equipped with a mechanical stirrer, thermometer and a condenser with a Dean-Stark trap was placed 5.7 grams squaric acid (0.05 mole), 12.5 grams (N,N-dimethylaniline (0.103 mole), 5 grams N,N-dimethy-2-fluoroaniline (0.036 mole) and 300 milliliters 1-heptanol. A vacuum of 20 Torr was applied by means of a gas inlet connecting tube at the top of the condenser. The mixture was heated with stirring to reflux at 90° C. The water formed during the course of the reaction was allowed to collect in the Dean-Stark trap. After 20 hours, the reaction was allowed to cool and was filtered. The blue crystalline pigment was washed with methanol and dried in vacuo at 50° C. Yield was 10.4 grams.

EXAMPLE XII

A siloxane layer was formed on an aluminized polyester film, Mylar, in which the aluminum had a thickness of about 250 Angstroms by applying a 0.22 percent (0.001 mole) solution of 3-aminopropyl triethoxylsilane to the aluminum layer with a Bird applicator. The deposited coating was dried in a forced air oven to form a dried coating having a thickness of 200 Angstroms. A coating of polyester resin, du Pont 49000, available from E. I. du Pont de Nemours & Co. was then applied with a Bird applicator to the dried silane layer. The polyester resin coating was dried to form a film having a thickness of about 0.5 micrometer. About 0.075 gram of the blue crystalline squaraine pigment of Example XVI was mixed in about 0.15 gram of a binder of Makrolon ®, (polycarbonate resin available from Farbenfabricken Bayer A.G.) and sufficient methylene chloride to form a 15 percent solids mixture. This mixture applied by means of a Bird applicator having a half mil gap to the polyester resin coating to form a coating. After drying in a forced air oven for 5 minutes at temperature of 135° C., the dried coating was found to have a thickness of about 0.5 micrometer. This squaraine generating layer was then overcoated with a charge transport layer containing about 50 percent by weight N,N'-diphenyl-N,N'-bis(3-methylphenyl)-1,1'-biphenyl-4,4'-diamine dispersed in about 50 percent by weight of Makrolon ® (polycarbonate resin available from Farbenfabricken Bayer A.G.). The charge transport layer had a thickness of 32 micron after drying. Electrical evaluation of the resulting coated device charged to about −1000 to −1200 volts revealed a dark decay of about 120 volts per second. Discharge when exposed to 10 ergs of activating radiation at a wavelength of about 800 nanometers was about 55 percent.

EXAMPLE XIII

Into a 1000 milliliter three-necked round bottom flask equipped with a mechanical stirrer, thermometer and a condenser with a Dean-Stark trap was placed 5.7 grams squaric acid (0.05 mole), 7 grams N,N-dimethyl-2-fluoroaniline (0.05 mole), and 300 milliliters 1-heptanol. A vacuum of 25 Torr was applied by means of a gas inlet connecting tube at the top of the condenser. The mixture was heated with stirring to reflux at 95° C. After 45 minutes the vacuum was broken and 14 grams N,N-dimethyl-3-fluoroaniline (0.089 mole) was added to the green solution. The vacuum was reapplied and the reaction heated with stirring to reflux for 18 hours. The reaction was allowed to cool and was filtered. The blue crystalline pigment was washed with methanol and dried in vacuuo at 50° C. Yield was 4.9 grams.

EXAMPLE XIV

A siloxane layer was formed on an aluminized polyester film, Mylar, in which the aluminum had a thickness of about 150 Angstroms by applying a 0.22 percent (0.001mole) solution of 3-aminopropyl triethoxylsilane to the aluminum layer with a Bird applicator. The deposited coating was dried in a forced air oven to form a dried coating having a thickness of 200 Angstroms. A coating of polyester resin, du Pont 49000, available from E. I. du Pont de Nemours & Co. was then applied with a Bird applicator to the dried silane layer. The polyester resin coating was dried to form a film having a thickness of about 0.5 micrometer. About 0.075 gram of the blue crystalline squaraine pigment of Example XIII was mixed in about 0.15 gram of a binder of Makrolon ®, (polycarbonate resin available from Farbenfabricken Bayer A.G.) and sufficient methylene chloride to form a 15 percent solids mixture. This mixture applied by means of a Bird applicator having a half mil gap to the polyester resin coating to form a coating. After drying in a forced air oven for 5 minutes at temperature of 135° C., the dried coating was found to have a thickness of about 0.5 micrometer. This squaraine generating layer was then overcoated with a charge transport layer containing about 50 percent by weight N,N'-diphenyl-N,N'-bis(3-methylphenyl)-1,1'-biphenyl-4,4'-diamine dispersed in about 50 percent by weight of Makrolon® (polycarbonate resin available from Farbenfabricken Bayer A.G.). The charge transport layer had a thickness of 32 micron after drying. Electrical evaluation of the resulting coated device charged to about −1000 to −1200 volts revealed a dark decay of about 160 volts per second. Discharge when exposed to 10 ergs of activating radiation at a wavelength of about 800 nanometers was about 65 percent.

EXAMPLE XV

Into a 3 liter three-necked round bottom flask equipped with a mechanical stirrer, thermometer and a condenser with a Dean-Stark trap was placed 28.5 grams squaric acid (0.25 mole), 77 grams N,N-dimethyl-m-toluidine (0.57 mole) and 1250 milliliters 1-heptanol. A vacuum of 47 Torr was applied by means of a gas inlet connecting tube at the top of the condenser. The mixture was heated with stirring to reflux at 105° C. The water formed during the course of the reaction was allowed to collect in the Dean-Stark trap. After 7 hours, the reaction was allowed to cool and was filtered. The green crystalline pigment was washed with methanol and dried in vacuuo at 50° C. Yield was 54 grams, 64 percent.

EXAMPLE XVI

A siloxane layer was formed on an aluminized polyester film, Mylar, in which the aluminum had a thickness of about 150 Angstroms by applying a 0.22 percent (0.001 mole) solution of 3-aminopropyl triethoxylsilane to the aluminum layer with a Bird applicator. The deposited coating was dried in a forced air oven to form a dried coating having a thickness of 200 Angstroms. A coating of polyester resin, du Pont 49000, available from E. I. du Pont de Nemours & Co. was then applied with a Bird applicator to the dried silane layer. The polyester resin was dried to form a film having a thickness of about 0.5 micrometer. About 0.075 gram of the green crystalline squaraine pigment of Example XV was mixed in about 0.15 gram of a binder of Makrolon®, (polycarbonate resin available from Farbenfabricken Bayer A.G.) and sufficient methylene chloride to form a 15 percent solids mixture. This mixture applied by means of a Bird applicator having a half mil gap to the polyester resin coating to form a coating. After drying in a forced air oven for 5 minutes at temperature of 135° C., the dried coating was found to have a thickness of about 0.5 micrometer. This squaraine generating layer was then overcoated with a charge transport layer containing about 50 percnt by weight N,N'-diphenyl-N,N'-bis(3-methylphenyl)-1,1'-biphenyl-4,4'-diamine dispersed in about 50 percent by weight of Makrolon® (polycarbonate resin available from Farbenfabricken Bayer A.G.). The charge transport layer had a thickness of 32 micron after drying. Electrical evaluation of the resulting coated device charged to about −1000 to −1200 volts revealed a dark decay of about 40 volts per second. Discharge when exposed to 10 ergs of activating radiation at a wavelength of about 800 nanometers was about 25 percent. This control example clearly demonstrates the improved sensitivity of the unsymmetrical squaraine reaction product of Example VII.

EXAMPLE XVII

Into a five liter three-necked round bottom flask equipped with a mechanical stirrer, thermometer and a condenser with a Dean-Stark trap was placed 114 grams squaric acid (1.0 mole), 280 grams N,N-dimethylaniline (2.3 moles), 2500 milliliters 1-hexanol. A vacuum of 100 Torr was applied by means of a gas inlet connecting tube at the top of the condenser. The mixture was heated with stirring to reflux at 125° C. The water formed during the course of the reaction was allowed to collect in the Dean-Stark trap. After 12 hours, the reaction was allowed to cool and was filtered. The blue crystalline pigment was washed with methanol and dried in vacuuo at 50° C. Yield was 128 grams, 40 percent.

EXAMPLE XVIII

A siloxane layer was formed on an aluminized polyester film, Mylar, in which the aluminum had a thickness of about 150 Angstroms by applying a 0.22 percent (0.001 mole) solution of 3-aminopropyl triethoxylsilane to the aluminum layer with a Bird applicator. The deposited coating was dried in a forced air oven to form a dried coating having a thickness of 200 Angstroms. A coating of polyester resin, du Pont 49000, available from E. I. du Pont de Nemours & Co. was then applied with a Bird applicator to the dried silane layer. The polyester resin coating was dried to form a film having a thickness of about 0.5 micrometer. About 0.075 gram of the blue crystalline squaraine pigment of Example XII was mixed in about 0.15 gram of a binder of Makrolon®, (polycarbonate resin available from Farbenfabricken Bayer A.G.) and sufficient methylene chloride to form a 15 percent solids mixture. This mixture applied by means of a Bird applicator having a half mil gap to the polyester resin coating to form a coating. After drying in a forced air oven for 5 minutes at temperature of 135° C., the dried coating was found to have a thickness of about 0.5 micrometer. This squaraine generating layer was then overcoated with a charge transport layer containing about 50 percent by weight N,N'-diphenyl-N,N'-bis(3-methylphenyl)-1,1'-biphenyl-4,4'-diamine dispersed in about 50 percent by weight of Makrolon® (polycarbonate resin available from Farbenfabricken Bayer A.G.). The charge transport layer had a thickness of 32 micron after drying. Electrical evaluation of the resulting coated device charged to about −1000 to −1200 volts revealed a dark decay of about 400+ volts per second. The rate of dark decay was too high to allow measurement of sensitivity. This control example clearly demonstrates the improved sensitivity of the unsymmetrical squaraine reaction product of Example VII.

Although the invention has been described with reference to specific preferred embodiments, it is not intended to be limited thereto, rather those skilled in the art will recognize that variations and modifications may be made therein which are within the spirit of the present invention and within the scope of the following claims.

We claim:

1. A process for synthesizing an unsymmetrical squaraine composition comprising forming a mixture comprising squaric acid, a primary alcohol having a boiling point between about 150° C. and about 190° C., a first tertiary amine having the formula:

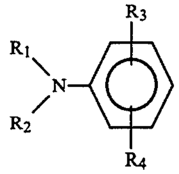

and a second tertiary amine having the formula:

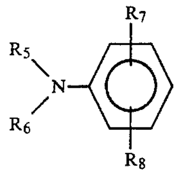

wherein $R_1$, $R_2$, $R_5$ and $R_6$ are independently selected from the group consisting of alkyl radicals having from 1 to 4 carbon atoms, phenyl radicals, and radicals having the formula:

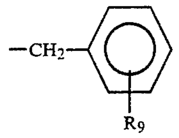

and $R_3$, $R_4$, $R_7$ and $R_8$ are independently selected from the group consisting of H, $CH_3$, $CH_2CH_3$, $CF_3$, F, Cl, Br, and COOH wherein at least one of $R_3$ and $R_4$ are different than $R_7$ and $R_8$ if $R_7$ and $R_8$ are located on the same relative position on the aromatic ring as $R_3$ and $R_4$ and wherein $R_9$ is selected from the group consisting of H, alkyl radicals having from 1 to 4 carbon atoms, F, Cl, Br, COOH, CN and $CF_3$, and heating said mixture in vacuo below the boiling points of said primary alcohols, said first tertiary amine and said second tertiary amine to form said unsymmetrical squaraine composition.

2. A process for synthesizing squaraines according to claim 1 wherein said mixture comprises about one mole of said squaric acid and about 1 mole to about 1.2 moles of said first tertiary amine and about 1 mole to about 1.2 moles of said second tertiary amine.

3. A process for synthesizing squaraines according to claim 1 including heating said solution in vacuo to a temperature between about 60° C. and about 130° C.

4. A process for synthesizing squaraines according to claim 2 wherein the pressure is maintained between about 5 torr and about 200 torr.

5. A process for synthesizing squaraines according to claim 1 wherein said long chain aliphatic alcohol comprises a mixture of long chain aliphatic alcohols.

6. A process for synthesizing squaraines according to claim 1 including introducing a strong acid to said solution prior to said heating of said solution.

7. An unsymmetrical squaraine having the formula:

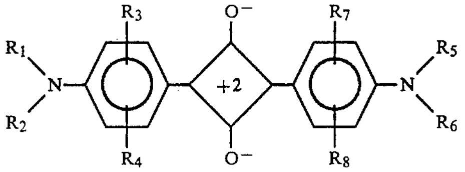

wherein $R_1$, $R_2$, $R_5$ and $R_6$ are independently selected from the group consisting of alkyl radicals having from 1 to 4 carbon atoms, phenyl radicals, and radicals having the formula:

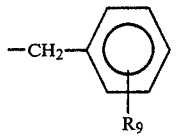

and $R_3$, $R_4$, $R_7$ and $R_8$ are independently selected from the group consisting of H, $CH_3$, $CH_2CH_3$, $CF_3$, F, Cl, Br, and COOH, wherein at least one of $R_3$ and $R_4$ are different than $R_7$ and $R_8$ if $R_7$ and $R_8$ are located on the same relative position on the aromatic ring as $R_3$ and $R_4$ and wherein $R_9$ is selected from the group consisting of H, alkyl radicals having from 1 to 4 carbon atoms, F, Cl, Br, COOH, CH and $CF_3$.

* * * * *